United States Patent
Grue-Sørensen et al.

[11] Patent Number: 5,554,599
[45] Date of Patent: Sep. 10, 1996

[54] 22-THIO VITAMIN D DERIVATIVES

[75] Inventors: Gunnar Grue-Sørensen, Ølstykke; Erik R. Uttosen, Copenhagen, both of Denmark

[73] Assignee: Leo Pharmaceutical Products Ltd., Ballerup, Denmark

[21] Appl. No.: 411,634

[22] PCT Filed: Dec. 17, 1993

[86] PCT No.: PCT/DK93/00425

§ 371 Date: Apr. 11, 1995

§ 102(e) Date: Apr. 11, 1995

[87] PCT Pub. No.: WO94/14766

PCT Pub. Date: Jul. 7, 1994

[30] Foreign Application Priority Data

Dec. 23, 1992 [GB] United Kingdom ............ 9226877

[51] Int. Cl.$^6$ .......................... A61K 31/59; C07C 401/00
[52] U.S. Cl. ................................. 514/167; 552/653
[58] Field of Search ................... 552/653; 514/167

[56] References Cited

FOREIGN PATENT DOCUMENTS

| 341158 | 11/1989 | European Pat. Off. ...... C07C 172/00 |
| 9527697 | 10/1995 | WIPO ........................... C07C 401/00 |

*Primary Examiner*—Kimberly J. Prior
*Attorney, Agent, or Firm*—Cushman Darby & Cushman, L.L.P.

[57] ABSTRACT

The present invention relates to compounds of the following formula

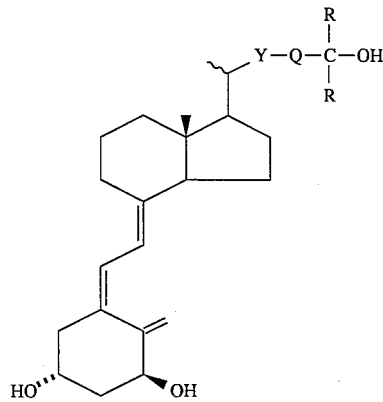

in which Y is sulfur, S(O), or S(O)$_2$; R stands for C$_1$–C$_3$ alkyl, or can form a C$_3$–C$_8$ carbocyclic ring. Q is a C$_1$–C$_8$ hydrocarbylene diradical; and derivatives thereof. The compounds can be made by reacting a 20(S)-formyl vitamin D derivative with tert-butyl hypochlorite to form the corresponding acid chloride which is then reacted with potassium O-ethyl dithiocarbonate followed by photochemical reaction and decarbonylation, treatment with aminoethanol, and conversion to the 22-thiol. The 22-thiol is then alkylated to form the desired sidechain. The compounds show antiinflammatory and immunomodulating effects. They also exhibit strong activity in inducing differentiation and inhibiting undesirable proliferation of certain cells.

13 Claims, No Drawings

22-THIO VITAMIN D DERIVATIVES

This application is a 371 of international application PCT/DK93/00425 filed Dec. 17, 1993.

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of hyperparathyroidism, particularly secondary hyperparathyroidism associated with renal failure, of a number of disease states including diabetes mellitus, hypertension, acne, alopecia, skin ageing, imbalance in the immune system, of inflammatory diseases such as rheumatoid arthritis and asthma, of diseases characterized by abnormal cell differentiation and/or cell proliferation such as e.g. psoriasis and cancer, for prevention and/or treatment of steroid induced skin atrophy, and for promoting osteogenesis and treating osteoporosis.

The compounds of the present invention are represented by the general formula I

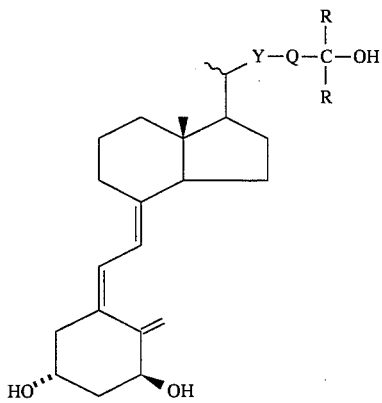

in which formula Y is sulfur, S(O), or S(O)$_2$; R stands for C$_1$–C$_3$ alkyl; or

can form a C$_3$–C$_8$ carbocyclic ring; Q is a C$_1$–C$_8$ hydrocarbylene diradical.

In the context of this invention, the expression hydrocarbylene diradical indicates the residue after removal of 2 hydrogen atoms from a straight, branched or cyclic, saturated or unsaturated hydrocarbon.

Examples of R include, but is not limited to, methyl, trifluoromethyl, ethyl, normal- and isopropyl.

Examples of Q include, but are not limited to, methylene, ethylene, tri-, tetra-, and pentamethylene, —CH=CH—, —CH$_2$—CH=CH—, —CH$_2$CH$_2$—CH=CH—, —CH$_2$—C≡C—, —CH$_2$CH$_2$—C≡C—, phenylene (C$_6$H$_4$; ortho, meta, para), —CH$_2$—(C$_6$H$_4$)— (ortho, meta, para), and —(C$_6$H$_4$)—CH$_2$— (ortho, meta, para).

The compounds of the invention comprise more than one stereoisomeric form (e.g., R or S configuration at C-20; E or Z configuration when a double bond is present in the group Q). The invention covers all these stereoisomers in pure form and mixtures thereof. In addition, prodrugs of I in which one or more of the hydroxy groups are masked as groups which can be reconverted to hydroxy groups in vivo are also within the scope of the invention.

It has been shown that 1α,25-dihydroxy-vitamin D$_3$ (1,25(OH)$_2$D$_3$) influences the effects and/or production of interleukins (Muller, K. et al., Immunol. Lett. 17, 361–366 (1988)), indicating the potential use of this compound in the treatment of diseases characterized by a dysfunction of the immune system, e.g. autoimmune diseases, AIDS, host versus graft reactions, and rejection of transplants or other conditions characterized by an abnormal interleukin-1 production, e.g. inflammatory diseases such as rheumatoid arthritis and asthma.

It has also been shown that 1,25(OH)$_2$D$_3$ is able to stimulate the differentiation of cells and inhibit excessive cell proliferation (Abe, E. et al., Proc. Natl. Acad. Sci., U.S.A. 78, 4990–4994 (1981)), and it has been suggested that this compound might be useful in the treatment of diseases characterized by abnormal cell proliferation and/or cell differentiation such as leukemia, myelofibrosis and psoriasis.

Also, the use of 1,25(OH)$_2$D$_3$, or its pro-drug 1α—OH—D$_3$, for the treatment of hypertension (Lind, L. et al., Acta Med. Scand. 222, 423–427 (1987)) and diabetes mellitus (Inomata, S. et al., Bone Mineral 1, 187–192 (1986)) has been suggested. Another indication for 1,25(OH)$_2$D$_3$ is suggested by the recent observation of an association between hereditary vitamin D resistance and alopecia: treatment with 1,25(OH)$_2$D$_3$ may promote hair growth (Editorial, Lancet, March 4, p. 478 (1989)). Also, the fact that topical application of 1,25(OH)$_2$D$_3$ reduces the size of sebaceous glands in the ears of male Syrian hamsters suggests that this compound might be useful for the treatment of acne (Malloy, V. L. et al., the Tricontinental Meeting for Investigative Dermatology, Washington, (1989)).

However, the therapeutic possibilities in such indications of 1,25(OH)$_2$D$_3$ are severely limited by the well known potent effect of this hormone on calcium metabolism; elevated blood concentrations will rapidly give rise to hypercalcemia. Thus, this compound and some of its potent synthetic analogues are not completely satisfactory for use as drugs in the treatment of e.g. psoriasis, leukemia or immune diseases which may require continuous administration of the drug in relatively high doses.

A number of vitamin D analogues have recently been described which show some degree of selectivity in favour of the cell differentiation inducing/cell proliferation inhibiting activity as compared with the effect on calcium metabolism.

A recent study (Colston, K. W. et al., Biochem. Pharmacol. 44, 693–702 (1992)) support the concept that vitamin D derivatives may inhibit breast cancer cell proliferation in vivo. Promising immunological properties of vitamin D analogues have been described (Binderup, L. Biochem. Pharmacol. 43, 1885–1892 (1992)).

A number of thia-analogues of vitamin D$_3$ are known. 23-Thia-analogues has been described (Kubodera, N. et al., Chem. Pharm. Bull. 39, 3221–3224 (1991) and European Patent Application number 78 704) and a series of 20R-23-thia-analogues have been reported in International Patent Application No. PCT/DK91/00091, filing date 22nd Mar. 1991, Publication No. WO 91/15475.

Furthermore, a series of 22-oxa-analogues of vitamin D$_3$ has been described (Murayama, E. et al., Chem. Pharm. Bull. 34, 4410–4413 (1986), Abe, J. et al., FEBS LETTERS 226, 58–62 (1987), European Patent Application No. 184 112, Binderup, L. et al., Biochem. Pharmacol. 42, 1569–1575 (1991) and International Patent Application No. PCT/DK90/00036, filing date 13th Feb. 1990, Publication No. 90/09991).

The fact that there are only small structural differences between the compounds of the prior art referred to above, but a large variation in their biological activities (cf. Binderup, L. et al., Biochem. Pharmacol. 42, 1569–1575 (1991)) implies that the present state of knowledge does not allow prediction of the structure of vitamin D analogues which will show a favourable degree of selectivity, as reflected by a higher cell differentiating activity in vitro compared to the binding affinity for intestinal vitamin D receptor in vitro. Furthermore, the matter is complicated by the fact that receptor binding affinities in vitro do not always follow those found by in vivo studies, probably reflecting a pharmacokinetic difference between the compounds.

The compounds of the present invention are 22-thia analogues of vitamin D and differ structurally from any known vitamin D analogues. Both analogues with the 20S and the 20R configuration are prepared by the methods of this invention. These compounds are highly active and show favourable selectivity. Thus, a particular compound of formula I is observed to show one or more of the following advantages when comparison to prior art is made:

(a) more potent effects on cell differentiation/proliferation;

(b) a greater selectivity in favour of the potent effects on cell differentiation/proliferation contra the effects on calcium metabolism;

(c) more potent effects on the production and action of interleukins;

(d) a greater selectivity in favour of the effects on interleukin production and action versus the effects on calcium metabolism;

(e) a longer metabolic half life.

The compounds of the invention are therefore especially suited for both local and systemic treatment and prophylaxis of human and veterinary disorders which are characterized by abnormal cell proliferation and/or cell differentiation, such as certain dermatological disorders including psoriasis and certain cancer forms, and/or by an imbalance in the immune system, e.g. in autoimmune diseases, including diabetes mellitus, host versus graft reaction, and rejection of transplants. The compounds of the invention are also suited for the treatment of inflammatory diseases, such as rheumatoid arthritis and asthma. Acne, alopecia, and hypertension are other conditions which may be treated with the compounds of the invention. Finally, as thickening of the skin is observed after topical treatment with the compounds of the invention, these compounds may be useful for treatment or prevention of skin ageing, including photo-ageing.

Because of the low tendency of the compounds to produce hypercalcemia on continued administration they are expected to be valuable for the long term treatment of hyperparathyroidism (particularly secondary hyperparathyroidism associated with renal failure) and for promoting osteogenesis and treating osteoporosis.

The present compounds may be used in combination with other pharmaceuticals. In the prevention of graft rejection and graft versus host reaction, a treatment with the present compounds may advantageously be combined with e.g. cyclosporin A treatment.

The compounds of formula I may conveniently be prepared from the vitamin D derivative 1 by the routes outlined in Scheme 1 or from the CD-ring derivative 78 by the routes outlined in Scheme 2.

The following standard abbreviations are used throughout this disclosure: Me=methyl; Et=ethyl; THP=tetrahydro-4H-pyran-2-yl; TMS=trimethylsilyl; pet.ether=petroleum ether; THF=tetrahydrofuran; TBAF=tetra-(n-butyl)ammonium fluoride trihydrate; Tf=trifluoromethane sulfonyl; DMF=N,N-dimethylformamide; "HF"=5% hydrogen fluoride in acetonitrile:water (7:1, v/v); TBDMS=tert-butyldimethylsilyl; PPTS=pyridinium toluene-4-sulfonate; DPMS=diphenylmethylsilyl; Ts=4-methylbenzenesulfonyl; DMSO=dimethylsulfoxide.

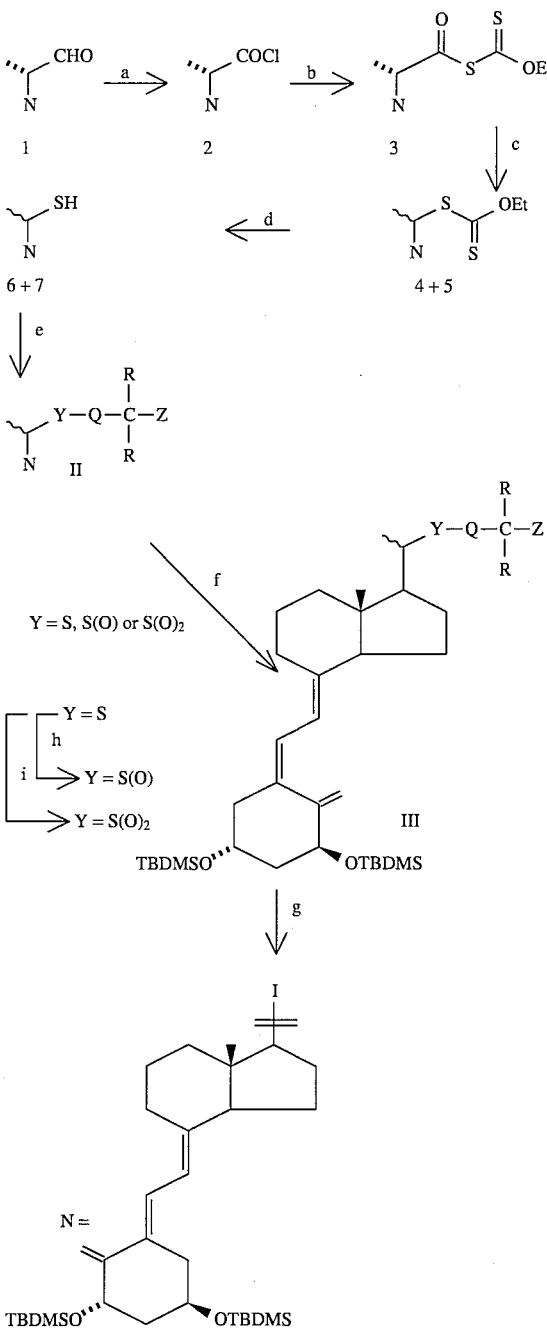

Scheme 1

Synthesis of the Compounds of Formula I

Q and R are defined as above, and Z is as defined in Notes.

Chromatographic separation of 20R and 20S isomers may be achieved after any of the steps d, e, f or g, preferably d, e or f. Chromatographic separation of sulfoxides with R and S configuration is achieved after step h.

Notes to Scheme 1
a) tert-Butyl hypochlorite/carbon tetrachloride/20–100 min
b) Potassium O-ethyl dithiocarbonate/acetone/–30° C./30 min and 20° C./60 min
c) Mercury lamp/benzene/60° C./10–40 min
d) Ethanolamine/DMF/10–60 min
e) IV (see below)/base, such as potassium carbonate/DMF/0.1–10 h or potassium hydride/18-Crown-6/THF/20–200 min
f) Mercury lamp/triplet sensitizer, e.g. anthracene/triethylamine/dichloromethane/10°–15° C./10–60 min
g) Deprotection of all alcohol groups with eg. "HF"/ethyl acetate/20–200 min or TBAF/THF/60° C./20–200 min or PPTS/EtOH/50° C./20–200 min
h) Sodium tungstate, dihydrate/1 eqv. hydrogen peroxide/sodium hydrogencarbonate/chloroform
i) Sodium tungstate, dihydrate/2 eqv. hydrogen peroxide/sodium hydrogencarbonate/chloroform

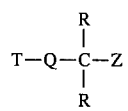

T⁻=leaving group, e.g. Br⁻, I⁻, TsO⁻, TfO⁻.

Z=OH or protected alcohol, such as TMS-O, TBDMS-O, DPMS-O or THP-O.

The synthesis of compounds 2–7 is described in the Preparations 1–4. The syntheses of the side chain building blocks IV are prepared by standard procedures described in the literature/International Patent Applications Nos. PCT/DK90/00036 and PCT/DK91/00091.

Scheme 2

Synthesis of the Compounds of Formula I

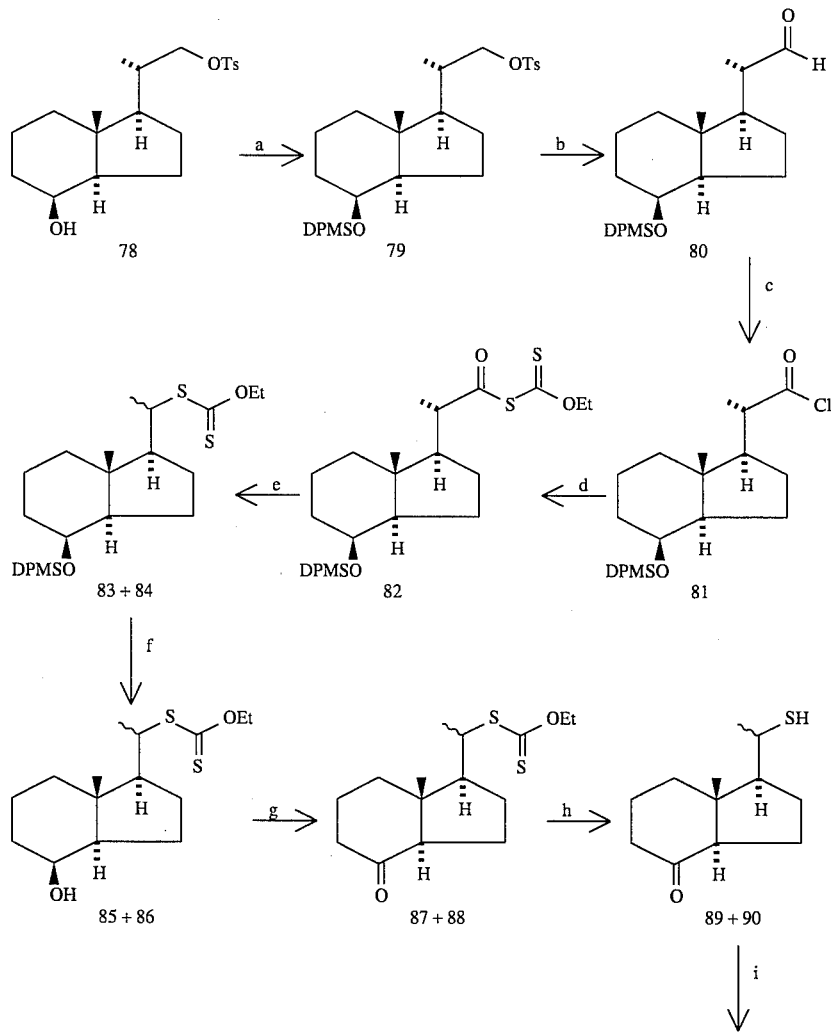

-continued
Scheme 2

Synthesis of the Compounds of Formula I

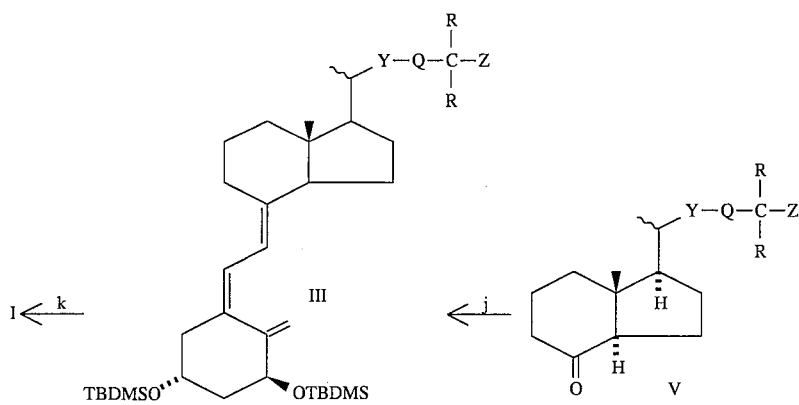

Q, R and Z are defined as above.

Notes to Scheme 2 a) DPMSCl/imidazole/DMF/20 h
b) 1 eqv. sodium hydrogencarbonate/DMSO/110° C./90 min
c) tert-Butyl hypochlorite/carbon tetrachloride/30–180 min
d) Potassium O-ethyl dithiocarbonate/acetone/–30° C./60 min and 20° C./60 min
e) Mercury lamp/benzene/60° C./10–40 min
f) "HF"/ethyl acetate/60 min
g) 1.1 eqv. Oxalylchloride/2.2 eqv. DMSO/dichloromethane/–65° C./5 min followed by compound 85 and 86/15 min
h) Ethanolamine/DMF/60 min
i) IV (see notes, Scheme 1)/base, such as potassium carbonate/DMF/0.1–10 h or potassium hydride/18-Crown- 6/THF/20–200 min
j) Compound 99 (see below)/n-butyl lithium/THF/–78° C./20 min/then V (see below)/THF/–78° C./120 min
k) Deprotection of all alcohol groups with eg. "HF"/ethyl acetate/20–200 min or TBAF/THF/60° C./20–200 min or PPTS/EtOH/50° C./20–200 min

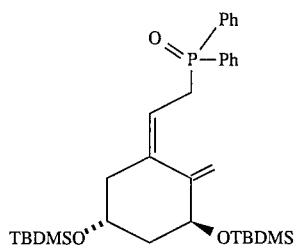

99

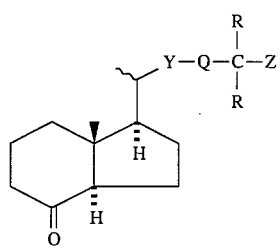

V

The synthesis of compounds 79–90 is described in the Preparations 58–67.

The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

For asthma treatment inhalation of powder, self-propelling or spray formulations, dispensed with a spray can, a nebulizer or an atomizer can be used. The formulations, when dispensed, preferably have a particle size in the range of 10 to 100μ.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$–$C_6$-alkyl hydrocarbons or halogenated $C_1$–$C_6$-alkyl hydrocarbons or mixtures thereof; chlorinated and fluorinated $C_1$–$C_6$-alkyl hydrocarbons are especially preferred. Generally, the propellant constitutes 45 to 99.9% w/w of the formulation whilst the active ingredient constitutes 0.1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including antioxidants), emulsifying agents and the like. The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1–100 μg, preferably from 0.2–25 μg, of a compound of formula I are administered. In the topical treatment of dermatological disorders, ointments, creams or lotions containing from 0.1–500 μg/g, and preferably from 0.1–100 μg/g, of a compound of formula I are administered. For topical use in ophthalmology ointments, drops or gels containing from 0.1–500 μg/g, and preferably from 0.1–100 μg/g, of a compound of formula I are administered. The oral compositions are formulated, preferably as tablets, capsules, or drops, containing from 0.05–50 μg, preferably from 0.1–25 μg, of a compound of formula I, per dosage unit.

The invention will now be further described in the following non-limiting General Procedures, Preparations and Examples:

General Procedures, Preparations and Examples

The exemplified compounds I are listed in Table 1, whereas compounds of the general formula II, III and V are listed in Table 2.

For $^1H$ nuclear magnetic resonance spectra (300 Mhz) chemical shift values (δ) are quoted, unless otherwise specified, for deuteriochloroform solutions relative to internal tetramethylsilane (δ=0.00) or chloroform (δ=7.25). The value for a multiplet, either defined (doublet (d), triplet (t), quartet (q)) or not (m) at the approximate mid point is given unless a range is quoted (s=singlet, b=broad).

Ether is diethyl ether, and was dried over sodium. THF was dried over sodium/benzophenone. Petroleum ether refers to the pentane fraction. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue. Chromatography was performed on silica gel.

TABLE 1

| Comp. No. | Example No. | General formula | conf. | Y | Q | R | X |
|---|---|---|---|---|---|---|---|
| 101 | 1 | I | R | S | $(CH_2)_2$ | Et | OH |
| 102 | 2 | I | S | S | $(CH_2)_2$ | Et | OH |
| 103 | 3 | I | R | S | $(CH_2)_3$ | Et | OH |
| 104 | 4 | I | S | S | $(CH_2)_3$ | Et | OH |
| 105 | 5 | I | R | S | $(CH_2)_4$ | Et | OH |
| 106 | 6 | I | S | S | $(CH_2)_4$ | Et | OH |
| 107 | 7 | I | R | S | $CH_2(m-C_6H_4)$ | Et | OH |

TABLE 1-continued

| Comp. No. | Example No. | General formula | 20 conf. | Y | Q | R | X |
|---|---|---|---|---|---|---|---|
| 108 | 8 | I | S | S | CH₂(m-C₆H₄) | Et | OH |
| 109 | 9 | I | R | S | CH₂CH=CH | Et | OH |
| 110 | 10 | I | S | S | CH₂CH=CH | Et | OH |
| 111 | 11 | I | R | S | CH₂C≡C | Et | OH |
| 112 | 12 | I | S | S | CH₂C≡C | Et | OH |
| 113 | 13 | I | R | S | (CH₂)₃ | Me | OH |
| 114 | 14 | I | S | S | (CH₂)₃ | Me | OH |
| 115 | 15 | I | R | S | (CH₂)₄ | Me | OH |
| 116 | 16 | I | S | S | (CH₂)₄ | Me | OH |
| 117 | 17 | I | R | S | CH₂(m-C₆H₄) | Me | OH |
| 118 | 18 | I | S | S | CH₂(m-C₆H₄) | Me | OH |
| 119 | 19 | I | R | S | CH₂CH=CH | Me | OH |
| 120 | 20 | I | S | S | CH₂CH=CH | Me | OH |
| 121 | 21 | I | R | S | CH₂C≡C | Me | OH |
| 122 | 22 | I | S | S | CH₂C≡C | Me | OH |
| 123 | 23 | I | R | S(O)* | (CH₂)₄ | Et | OH |
| 124 | 24 | I | R | S(O)¤ | (CH₂)₄ | Et | OH |
| 125 | 25 | I | S | S(O)* | (CH₂)₄ | Et | OH |
| 126 | 26 | I | S | S(O)¤ | (CH₂)₄ | Et | OH |
| 127 | 27 | I | R | S(O)₂ | (CH₂)₄ | Et | OH |
| 128 | 28 | I | S | S(O)₂ | (CH₂)₄ | Et | OH |
| 129 | 29 | I | R | S(O)* | CH₂(m-C₆H₄) | Me | OH |
| 130 | 30 | I | R | S(O)¤ | CH₂(m-C₆H₄) | Me | OH |
| 131 | 31 | I | S | S(O)* | CH₂(m-C₆H₄) | Me | OH |
| 132 | 32 | I | S | S(O)¤ | CH₂(m-C₆H₄) | Me | OH |
| 133 | 33 | I | R | S(O)₂ | CH₂(m-C₆H₄) | Me | OH |
| 134 | 34 | I | S | S(O)₂ | CH₂(m-C₆H₄) | Me | OH |
| 135 | 35 | I | R | S | (CH₂)₂ | Me | OH |
| 136 | 36 | I | S | S | (CH₂)₂ | Me | OH |

*This compound has arbitrarily been given the R-configuration at the sulfur atom.
¤This compound has arbitrarily been given the S-configuration at the sulfur atom.

TABLE 2

| Comp. No. | Prep. No. | General formula | 20 conf. | Y | Q | R | X |
|---|---|---|---|---|---|---|---|
| 8 | 5 | II | R | S | (CH₂)₂ | Et | OH |
| 9 | 5 | II | S | S | (CH₂)₂ | Et | OH |
| 10 | 6 | II | R | S | (CH₂)₃ | Et | OH |
| 11 | 6 | II | S | S | (CH₂)₃ | Et | OH |
| 12 | 7 | II | R | S | (CH₂)₄ | Et | OH |
| 13 | 7 | II | S | S | (CH₂)₄ | Et | OH |
| 14 | 8 | II | R | S | CH₂(m-C₆H₄) | Et | OH |
| 15 | 8 | II | S | S | CH₂(m-C₆H₄) | Et | OH |
| 16 | 9 | II | R | S | CH₂CH=CH | Et | OH |
| 17 | 9 | II | S | S | CH₂CH=CH | Et | OH |
| 18 | 10 | II | R | S | CH₂C≡C | Et | OH |
| 19 | 10 | II | S | S | CH₂C≡C | Et | OH |
| 20 | 11 | II | R | S | (CH₂)₃ | Me | OH |
| 21 | 11 | II | S | S | (CH₂)₃ | Me | OH |
| 22 | 12 | II | R | S | (CH₂)₄ | Me | OH |
| 23 | 12 | II | S | S | (CH₂)₄ | Me | OH |
| 24 | 13 | II | R | S | CH₂(m-C₆H₄) | Me | OH |
| 25 | 13 | II | S | S | CH₂(m-C₆H₄) | Me | OH |
| 26 | 14 | II | R | S | CH₂CH=CH | Me | OH |
| 27 | 14 | II | S | S | CH₂CH=CH | Me | OH |
| 28 | 15 | II | R | S | CH₂C≡C | Me | OH |
| 29 | 15 | II | S | S | CH₂C≡C | Me | OH |
| 30, 31 | 16 | II | R | S(O)# | (CH₂)₄ | Et | OH |
| 32, 33 | 17 | II | S | S(O)# | (CH₂)₄ | Et | OH |
| 34 | 18 | II | R | S(O)₂ | (CH₂)₄ | Et | OH |
| 35 | 19 | II | S | S(O)₂ | (CH₂)₄ | Et | OH |
| 36, 37 | 20 | II | R | S(O)# | CH₂(m-C₆H₄) | Me | OH |
| 38, 39 | 21 | II | S | S(O)# | CH₂(m-C₆H₄) | Me | OH |
| 40 | 22 | II | R | S(O)₂ | CH₂(m-C₆H₄) | Me | OH |
| 41 | 23 | II | S | S(O)₂ | CH₂(m-C₆H₄) | Me | OH |
| 42 | 24 | III | R | S | (CH₂)₂ | Et | OH |
| 43 | 25 | III | S | S | (CH₂)₂ | Et | OH |
| 44 | 26 | III | R | S | (CH₂)₃ | Et | OH |
| 45 | 27 | III | S | S | (CH₂)₃ | Et | OH |
| 46 | 28 | III | R | S | (CH₂)₄ | Et | OH |
| 47 | 29 | III | S | S | (CH₂)₄ | Et | OH |
| 48 | 30 | III | R | S | CH₂(m-C₆H₄) | Et | OH |
| 49 | 31 | III | S | S | CH₂(m-C₆H₄) | Et | OH |
| 50 | 32 | III | R | S | CH₂CH=CH | Et | OH |
| 51 | 33 | III | S | S | CH₂CH=CH | Et | OH |
| 52 | 34 | III | R | S | CH₂C≡C | Et | OH |
| 53 | 35 | III | S | S | CH₂C≡C | Et | OH |
| 54 | 36 | III | R | S | (CH₂)₃ | Me | OH |
| 55 | 37 | III | S | S | (CH₂)₃ | Me | OH |
| 56 | 38 | III | R | S | (CH₂)₄ | Me | OH |
| 57 | 39 | III | S | S | (CH₂)₄ | Me | OH |
| 58 | 40 | III | R | S | CH₂(m-C₆H₄) | Me | OH |
| 59 | 41 | III | S | S | CH₂(m-C₆H₄) | Me | OH |
| 60 | 42 | III | R | S | CH₂CH=CH | Me | OH |
| 61 | 43 | III | S | S | CH₂CH=CH | Me | OH |
| 62 | 44 | III | R | S | CH₂C≡C | Me | OH |
| 63 | 45 | III | S | S | CH₂C≡C | Me | OH |
| 64 | 46 | III | R | S(O)* | (CH₂)₄ | Et | OH |
| 65 | 47 | III | R | S(O)¤ | (CH₂)₄ | Et | OH |
| 66 | 48 | III | S | S(O)¤ | (CH₂)₄ | Et | OH |
| 67 | 49 | III | S | S(O)¤ | (CH₂)₄ | Et | OH |
| 68 | 50 | III | R | S(O)₂ | (CH₂)₄ | Et | OH |
| 69 | 51 | III | S | S(O)₂ | (CH₂)₄ | Et | OH |
| 70 | 52 | III | R | S(O)* | CH₂(m-C₆H₄) | Me | OH |
| 71 | 53 | III | R | S(O)¤ | CH₂(m-C₆H₄) | Me | OH |
| 72 | 54 | III | S | S(O)* | CH₂(m-C₆H₄) | Me | OH |
| 73 | 55 | III | S | S(O)¤ | CH₂(m-C₆H₄) | Me | OH |
| 74 | 56 | III | R | S(O)₂ | CH₂(m-C₆H₄) | Me | OH |
| 75 | 57 | III | S | S(O)₂ | CH₂(m-C₆H₄) | Me | OH |
| 76 | 58 | III | R | S | (CVH₂)₂ | Me | OH |
| 77 | 58 | III | S | S | (CH₂)₂ | Me | OH |
| 91 | 68 | V | R | S | (CH₂)₂ | Me | OH |
| 92 | 68 | V | S | S | (CH₂)₂ | Me | OH |
| 93 | 69 | V | R | S | (CH₂)₄ | Me | OH |
| 94 | 69 | V | S | S | (CH₂)₄ | Me | OH |
| 95 | 70 | V | R | S | CH₂(m-C₆H₄) | Me | OH |
| 96 | 70 | V | S | S | CH₂(m-C₆H₄) | Me | OH |
| 56 | 71 | III | R | S | (CH₂)₄ | Me | OH |
| 57 | 71 | III | S | S | (CH₂)₄ | Me | OH |
| 58 | 72 | III | R | S | CH₂(m-C₆H₄) | Me | OH |
| 59 | 72 | III | S | S | CH₂(m-C₆H₄) | Me | OH |

A mixture of compounds with R- and S-configuration at the sulfur atom is produced by this reaction. These isomers are readily separated by chromatography.
*This compound has arbitrarily been given the R-configuration at the sulfur atom.
¤This compound has srbitrarily been given the S-configuration at the sulfur atom.

The synthetic sequence depicted in Scheme 1 leading to a mixture of compound 6 and 7 was carried out without strict purification of all intermediates 2, 3, 4 and 5. The spectroscopic data given for each of these compounds are obtained from purified samples.

Preparation 1: 1(S),3(R)-Bis-[tert-butyldimethylsilyl oxy]-20(S)-chlorocarbonyl-9,10-secopregna-5 (Z),7(E),10(19)-triene (Compound 2)

Compound 1 (3.54 g) (Calverley, M. C., Tetrahedron 43, 4609–4619 (1987)) was dissolved in carbon tetrachloride (35 ml) and tert-butyl hypochlorite (1.00 ml) was added at ambient temperature. After stirring for 30 min under argon the reaction mixture was concentrated in vacuo to yield the title compound as an oil.

NMR (CCl₄): δ=0.10 (m, 12H), 0.64 (s, 3H), 0.90 (s, 9H), 0.94 (s, 9H), 1.41 (d, 3H), 1.30–2.25 (m, 13H), 2.32 (bd, 1H), 2.53 (dd, 1H), 2.82 (m, 1H), 2.94 (m, 1H), 4.23 (m, 1H), 4.50 (m, 1H), 4.92 (m, 1H), 4.94 (m, 1H), 5.81 (d, 1H), 6.36 (d, 1H).

Preparation 2: 1(S),3(R)-Bis-[tert-butyldimethylsilyloxy]-20 (S)-O-[[ethyloxy(thiocarbonyl)thio]carbonyl]-9,10-secopregna- 5(Z),7(E),10(19)-triene (Compound 3)

The crude compound 2 (4.22 g) was dissolved in acetone (35 ml) and potassium O-ethyl dithiocarbonate (1.09 g) was added while stirring at −30° C. under argon. Stirring was continued for 30 min. The reaction mixture was allowed to reach room temperature and after 60 min the reaction mixture was washed with saturated aqueous sodium hydrogen-carbonate and worked up (dichloromethane) to yield the title compound.

NMR: δ=0.05 (m, 12H), 0.54 (s, 3H), 0.86 (s, 9H), 0.90 (s, 9H), 1.27 (d, 3H), 1.47 (t, 3H), 1.15–2.00 (m, 12H), 2.05 (bt, 1H), 2.28 (bd, 1H), 2.52 (m, 1H), 2.55 (dd, 1H), 2.87 (m, 1H), 4.21 (m, 1H), 4.52 (m, 1H), 4.67 (q, 2H), 4.94 (m, 1H), 4.98 (m, 1H), 5.82 (d, 1H), 6.43 (d, 1H).

Preparation 3: 1(S),3(R)-Bis-[tert-butyldimethylsilyloxy]-20(S)/20(R)-O-ethylxanthogenato-9,10-secopregna- 5(Z), 7(E),10(19)-triene (Compound 4 and 5)

The crude compound 3 (4.45 g) was dissolved in benzene (150 ml) in a Pyrex flask under argon. The reaction mixture was heated to 60° C. and was irradiated with UV-light from a high pressure ultraviolet lamp, type TQ760Z2 (Hanau) for 20 min under stirring. The reaction mixture was concentrated in vacuo and purified by chromatography (dichloromethane/pet. ether: 1/3 ) to yield the title compounds.

NMR (4): δ=0.06 (m, 12H), 0.64 (s, 3H), 0.86 (s, 9H), 0.89 (s, 9H), 1.42 (t, 3H), 1.48 (d, 3H), 1.20–1.82 (m, 9H), 1.85–2.15 (m, 4H), 2.29 (bd, 1H), 2.56 (dd, 1H), 2.88 (dd, 1H), 3.76 (m, 1H), 4.21 (m, 1H), 4.53 (m, 1H), 4.64 (m, 2H), 4.94 (m, 1H), 4.98 (m, 1H), 5.82 (d, 1H), 6.44 (d, 1H) .

NMR (5): δ=0.06 (m, 12H), 0.58 (s, 3H), 0.85 (s, 9H), 0.89 (s, 9H), 1.41 (d, 3H), 1.42 (t, 3H), 1.15–2.15 (m, 12H), 2.25 (bd, 1H), 2.29 (bd, 1H), 2.55 (dd, 1H), 2.87 (m, 1H), 3.65 (m, 1H), 4.21 (m, 1H), 4.52 (m, 1H), 4.63 (q, 2H), 4.94 (m, 1H), 4.98 (m, 1H), 5.81 (d, 1H), 6.44 (d, 1H).

Preparation 4: 1(S),3(R)-Bis-[tert-butyldimethylsilyloxy]-20(S)/20(R)-mercapto-9,10-secopregna- 5(Z),7(E),10(19)-triene (Compound 6 and 7)

To a solution of compound 4 and 5 (550 mg) in dry N,N-dimethylformamide (6.0 ml) was added aminoethanol (0.75 ml) under argon and with stirring. Stirring was continued for 30 min at ambient temperature. The reaction mixture was worked up (diethyl ether). The residue was purified by chromatography (diethyl ether/pet.ether: 1/20) to yield a mixture of the title compounds.

NMR (6): δ=0.06 (m, 12H), 0.55 (s, 3H), 0.85 (s, 9H), 0.90 (s, 9H), 1.41 (d, 3H), 1.15–2.47 (m, 15H), 2.55 (dd, 1H), 2.86 (bd, 1H), 2.94 (m, 1H), 4.21 (m, 1H), 4.52 (m, 1H), 4.93 (m, 1H), 4.98 (m, 1H), 5.82 (d, 1H), 6.44 (d, 1H).

NMR (7): δ=0.06 (m, 12H), 0.59 (s, 3H), 0.86 (s, 9H), 0.90 (s, 9H), 1.51 (d, 3H), 1.15–2.47 (m, 15H), 2.55 (dd, 1H), 2.80–3.05 (m, 2H), 4.21 (m, 1H), 4.52 (m, 1H), 4.93 (m, 1H), 4.98 (m, 1H), 5.82 (d, 1H), 6.44 (d, 1H).

General Procedure 1: Alkylation of compounds 6 and/or 7 to compounds of the general formula II To a solution stirred under argon of compound 6 and/or 7 (1.0 mmol) and 18-Crown-6 (0.5 mmol) in dry THF (10 ml) was added potassium hydride (1,5 mmol, 20% i oil) followed by the requisite alkylating agent IV (2.0 mmol). The mixture was stirred for 45 min at ambient temperature and then quenched with a few drops of water. The reaction mixture was worked up (diethyl ether) and the residue purified by chromatography to yield the separated title compounds.

General Procedure 2: Alkylation of compounds 6 and/or 7 to compounds of the general formula II A solution of 6 and/or 7 (1.25 mmol) was stirred with solid potassium carbonate (1.6 mmol) for 15 min in DMF (5 ml). The requisite alkylating agent IV (1.5 mmol) in DMF (3 ml) was added and the mixture was stirred for 3 h. Work up (diethyl ether) and chromatography gave the separated title compounds.

General Procedure 3: Isomerization of compounds of the general formula II to compounds of the general formula III A solution of a compound of the general formula II (0.1 mmol), anthracene (0.2 mmol) and triethylamine (0.05 ml) in dichloromethane (4.0 ml) under argon in a Pyrex flask was irradiated with UV-light from a high pressure ultraviolet lamp, type TQ760Z2 (Hanau) at ca. 10° C. for 20 min under stirring. The reaction mixture was concentrated in vacuo and treated with pet.ether (2×5 ml). After filtering the filtrate was concentrated in vacuo and purified by chromatography (mixture of dichloromethane and pet.ether as eluant) to yield the title compound.

General Procedure 4: Deprotection of compounds with the general formula III to the corresponding compounds I by treatment with "HF"

To a solution of a compound with the general formula III (0.05 mmol) in ethyl acetate (0.25 ml) was added acetonitrile (1.0 ml) followed by a 5% solution of hydrofluoric acid in acetonitrile:water, 7:1 (0.8 ml) under argon and with stirring. Stirring was continued for 45 min at ambient temperature. Saturated aqueous sodium hydrogen-carbonate (10 ml) was added, and the reaction mixture was worked up (ethyl acetate). The residue was purified by chromatography (ethyl acetate as eluant) to yield the title compound.

General Procedure 5: Deprotection of compounds of the general formula III to the corresponding compounds I by treatment with tetra-n-butylammonium fluoride To a solution of a compound of the general formula III (0.16 mmol) in THF (5 ml), a solution of TBAF (300 mg) in THF (5 ml) was added while stirring at 60° C. under argon. Stirring was continued for one hour at 60° C., the reaction mixture was washed with saturated aqueous sodium hydrogen-carbonate and worked up (ethyl acetate). The residue was purified by chromatography (ethyl acetate as eluant) to yield the title compound.

General Procedure 6: Deprotection of compounds with the general formula III to the corresponding compounds I by treatment with pyridinium toluene-4-sulfonate PPTS (2 mg) was added to a solution of a compound with the general formula III (0.16 mmol) in 99% ethanol (2 ml), and the mixture was stirred at 50° C. under argon for one hour. The mixture was washed with saturated aqueous sodium hydrogen-carbonate and worked up (ethyl acetate). The crude product was purified by chromatography (ethyl acetate as eluant) to give the title compound.

General Procedure 7: Oxidation of 22-thia compounds of the general formula II to the corresponding isomeric sulfoxides also of the general formula II To a mixture of a 22-thia compound of the general formula II (0.15 mmol), sodium hydrogen carbonate (10 mg), a 2% (w/v) solution of sodium tungstate, dihydrate (10 μl) and methanol (0.5 ml) was added 30% hydrogenperoxide (24 μl) and chloroform (0.5 ml). After stirring at the appropriate temperature for several hours water was added and the mixture worked up (dichloromethane) to give a residue which was chromatographed to separate the pure 22(R)- and 22(S)-sulfoxides.

General Procedure 8: Oxidation of 22-thionyl compounds of the general formula II to the corresponding sulfonyl compounds also of the general formula II To a mixture of a 22-thionyl compound 22(R) and/or 22(S) of the general formula II (0.15 mmol), sodium hydrogen carbonate (30 mg), a 2% (w/v) solution of sodium tungstate, dihydrate (30 µl) and methanol (0.6 ml) was added hydrogenperoxide (36 µl). After stirring at the appropriate temperature for several hours water was added and the mixture worked up (dichloromethane) to give a residue which was chromatographed to give the title compound.

General procedure 9: Alkylation of compounds 89 and/or 90 to compounds of the general formula V A solution of compound 89 and/or 90 (0.75 mmol) was stirred with solid potassium carbonate (0.76 mmol) for 15 min in DMF (5 ml) under argon. The requisite alkylating agent IV (1.13 mmol) in DMF (5 ml) was added and the mixture was stirred for 3 h. Work up (diethyl ether) and chromatography gave the title compounds.

General procedure 10: Coupling of compounds of the general formula V with [1Z,3S,5R]-[2-[3,5Bis-[tert-butyldimethylsilyloxy]-2-methylenecyclohexylidene]ethyl]diphenylphosphine oxide, (compound 99) to compounds of the general formula III A solution of compound 99 (0.60 mmol) (Baggiolini, G. H. et al, J.Org.Chem. 51, 3098–3108 (1986)) in THF (7 ml) was cooled to −78° C. under argon and with stirring. n-Butyl lithium (0.60 mmol, 1.6M in hexane) was added over a few minutes and the resulting deep red solution was allowed to stir for another 20 min. Compounds of the general formula V (0.50 mmol, in 3 ml THF) were then added within 5 min to the reaction mixture. The mixture was stirred for 2 h and was then allowed to come to room temperature. It was quenched with a drop of water and worked up (ethyl acetate/pet.ether: 1/1). The residue was purified by chromatography (mixture of dichloromethane and pet.ether as eluant) to yield the separated title compounds.

Preparation 5: Compound 8 and 9
  Method: General Procedure 1.
  Alkylating agent: 5-Bromo-3-ethyl-3-trimethylsilyloxypentane (0.5

Preparation 6: Compound 10 and 11
  Method: General Procedure 1.
  Alkylating agent: 6-Bromo-3-ethyl-3-trimethylsilyloxyhexane (0.5 g).
  NMR (10): δ=0.05 (m, 12H), 0.09 (s, 9H), 0.62 (s, 3H), 0.80 (t, 6H), 0.85 (s, 9H), 0.90 (s, 9H), 1.28 (d, 3H), 1.45 (q, 4H), 1.15–2.15 (m, 17H), 2.30 (bd, 1H), 2.47 (m, 2H), 2.55 (dd, 1H), 2.66 (m, 1H), 2.87 (m, 1H), 4.21 (m, 1H), 4.52 (m, 1H), 4.94 (m, 1H), 4.98 (m, 1H), 5.81 (d, 1H), 6.45 (d, 1H).
  NMR (11): δ=0.05 (m, 12H), 0.09 (s, 9H), 0.57 (s, 3H), 0.81 (t, 6H), 0.85 (s, 9H), 0.89 (s, 9H), 1.38 (d, 3H), 1.46 (q, 4H), 1.15–2.17 (m, 17H), 2.29 (bd, 1H), 2.50 (m, 2H), 2.56 (dd, 1H), 2.65 (m, 1H), 2.87 (m, 1H), 4.21 (m, 1H), 4.52 (m, 1H), 4.94 (m, 1H), 4.98 (m, 1H), 5.82 (d, 1H), 6.44 (d, 1H).

Preparation 7: Compound 12 and 13
  Method: General Procedure 1.
  Alkylating agent: 7-Bromo-3-ethyl-3-trimethylsilyloxyheptane.

Preparation 8: Compound 14 and 15
  Method: General Procedure 2.
  Alkylating agent: 3-(1-Ethyl-1-hydroxypropyl)benzyl bromide.

Preparation 9: Compound 16 and 17
  Method: General Procedure 1.
  Alkylating agent: 6-Bromo-3-ethyl-3-trimethylsilyloxyhex-4-ene.

Preparation 10: Compound 18 and 19
  Method: General Procedure 1.
  Alkylating agent: 6-Bromo-3-ethyl-3-trimethylsilyloxyhex-4-yne.

Preparation 11: Compound 20 and 21
  Method: General Procedure 1.
  Alkylating agent: 5-Bromo-2-methyl-2-trimethylsilyloxypentane.

Preparation 12: Compound 22 and 23
  Method: General Procedure 1.
  Alkylating agent: 6-Bromo-2-methyl-2-tetrahydropyranyloxyhexane.

Preparation 13: Compound 24 and 25
  Method: General Procedure 2.
  Alkylating agent: 3-(1-Methyl-1-hydroxyethyl)benzyl bromide.

Preparation 14: Compound 26 and 27
  Method: General Procedure 1.
  Alkylating agent: 5-Bromo-2-methyl-2-trimethylsilyloxypent-4-ene.

Preparation 15: Compound 28 and 29
  Method: General Procedure 1.
  Alkylating agent: 5-Bromo-2-methyl-2-trimethylsilyloxypent-4-yne.

Preparation 16: Compound 30 and 31
  Method: General procedure 7.

Preparation 17: Compound 32 and 33
  Method: General procedure 7.

Preparation 18: Compound 34
  Method: General procedure 8.

Preparation 19: Compound 35
  Method: General procedure 8.

Preparation 20: Compound 36 and 37
  Method: General procedure 7.

Preparation 21: Compound 38 and 39
  Method: General procedure 7.

Preparation 22: Compound 40
  Method: General procedure 8.

Preparation 23: Compound 41
  Method: General procedure 8.

Preparation 24: Compound 42
  Method: General Procedure 3.
  Starting material: Compound 8.

Preparation 25: Compound 43
  Method: General Procedure 3.
  Starting material: Compound 9.

Preparation 26: Compound 44
  Method: General Procedure 3.
  Starting material: Compound 10.
  NMR: δ=0.05 (m, 12H), 0.08 (s, 9H), 0.60 (s, 3H), 0.81 (m, 6H), 0.86 (s, 18H), 1.27 (d, 3H), 1.45 (q, 4H), 1.15–2.15 (m, 17H), 2.21 (dd, 1H), 2.37–2.57 (m, 3H), 2.65 (m, 1H), 2.82 (m, 1H), 4.18 (m, 1H), 4.36 (m, 1H), 4.85 (m, 1H), 5.17 (m, 1H), 6.00 (d, 1H), 6.23 (d, 1H).

Preparation 27: Compound 45
  Method: General Procedure 3.
  Starting material: Compound 11.
  NMR: δ=0.05 (m, 12H), 0.09 (s, 9H), 0.55 (s, 3H), 0.81 (t, 6H), 0.86 (s, 18H), 1.37 (d, 3H), 1.45 (q, 4H), 1.15–2.14 (m, 17H), 2.21 (dd, 1H), 2.44 (dd, 1H), 2.48 (m, 2H), 2.64 (m, 1H), 2.82 (m, 1H), 4.18 (m, 1H), 4.36 (m, 1H), 4.85 (m, 1H), 5.17 (m, 1H), 6.01 (d, 1H), 6.22 (d, 1H).

Preparation 28: Compound 46
  Method: General Procedure 3.
  Starting material: Compound 12.

Preparation 29: Compound 47
  Method: General Procedure 3.
  Starting material: Compound 13.

Preparation 30: Compound 48
  Method: General Procedure 3.
  Starting material: Compound 14.

Preparation 31: Compound 49

Method: General Procedure 3.
Starting material: Compound 15.
Preparation 32: Compound 50
Method: General Procedure 3.
Starting material: Compound 16.
Preparation 33: Compound 51
Method: General Procedure 3.
Starting material: Compound 17.
Preparation 34: Compound 52
Method: General Procedure 3.
Starting material: Compound 18.
Preparation 35: Compound 53
Method: General Procedure 3.
Starting material: Compound 19.
Preparation 36: Compound 54
Method: General Procedure 3.
Starting material: Compound 20.
Preparation 37: Compound 55
Method: General Procedure 3.
Starting material: Compound 21.
Preparation 38: Compound 56
Method: General Procedure 3.
Starting material: Compound 22.
Preparation 39: Compound 57
Method: General Procedure 3.
Starting material: Compound 23.
Preparation 40: Compound 58
Method: General Procedure 3.
Starting material: Compound 24.
Preparation 41: Compound 59
Method: General Procedure 3.
Starting material: Compound 25.
Preparation 42: Compound 60
Method: General Procedure 3.
Starting material: Compound 26.
Preparation 43: Compound 61
Method: General Procedure 3.
Starting material: Compound 27.
Preparation 44: Compound 62
Method: General Procedure 3.
Starting material: Compound 28.
Preparation 45: Compound 63
Method: General Procedure 3.
Starting material: Compound 29.
Preparation 46: Compound 64
Method: General Procedure 3.
Starting material: Compound 30.
Preparation 47: Compound 65
Method: General Procedure 3.
Starting material: Compound 31.
Preparation 48: Compound 66
Method: General Procedure 3.
Starting material: Compound 32.
Preparation 49: Compound 67
Method: General Procedure 3.
Starting material: Compound 33.
Preparation 50: Compound 68
Method: General Procedure 3.
Starting material: Compound 34.
Preparation 51: Compound 69
Method: General Procedure 3.
Starting material: Compound 35.
preparation 52: Compound 70
Method: General Procedure 3.
Starting material: Compound 36.
Preparation 53: Compound 71
Method: General Procedure 3.
Starting material: Compound 37.
Preparation 54: Compound 72
Method: General Procedure 3.
Starting material: Compound 38.
Preparation 55: Compound 73
Method: General Procedure 3.
Starting material: Compound 39.
Preparation 56: Compound 74
Method: General Procedure 3.
Starting material: Compound 40.
Preparation 57: Compound 75
Method: General Procedure 3.
Starting material: Compound 41.
Preparation 58: Compound 76 and 77
Method: General Procedure 10.
Starting material: Compound 91 and 92.

NMR (76): $\delta$=0.05 (m, 12H), 0.10 (s, 9H), 0.60 (s, 3H), 0.87 (s, 18H), 1.22 (s, 6H), 1.28 (d, 3H), 1.10–2.05 (m, 15H), 2.20 (dd, 1H), 2.40–2.60 (m, 3H), 2.66 (m, 1H), 2.82 (m, 1H), 4.18 (m, 1H), 4.37 (m, 1H), 4.85 (m, 1H), 5.17 (m, 1H), 6.00 (d, 1H), 6.23 (d, 1H)

NMR (77): $\delta$=0.05 (m, 12H), 0.10 (s, 9H), 0.56 (s, 3H), 0.87 (s, 18H), 1.22 (s, 6H), 1.37 (d, 3H), 1.10–2.10 (m, 15H), 2.20 (dd, 1H), 2.44 (dd, 1H), 2.55 (m, 2H), 2.65 (m, 1H), 2.82 (m, 1H), 4.17 (m, 1H), 4.36 (m, 1H), 4.85 (m, 1H), 5.17 (m, 1H), 6.01 (d, 1H), 6.22 (d, 1H).

Preparation 60: 20(S)-(4-methylbenzenesulfonyloxymethyl)- 8(S)-(methyldiphenylsilyloxy)-de-A,B-pregnane (compound 79)

Compound 78 (15.9 g) (Lythgoe, B. et al, J.Chem.Soc., Perkin Trans.1, 2608–2612 (1977)) and imidazole (7.39 g) was dissolved in DMF (250 ml). Diphenyimethylchlorosilane (11.9 ml) was added and the reaction mixture was stirred 20 h under argon. The reaction mixture was partitioned between water/ice and diethyl ether. The organic phase was washed with hydrochloric acid (1N) and worked up. The residue was purified by chromatography (ethyl acetate/pet.ether: 1/10) to yield the title compound.

NMR: $\delta$=0.62 (s, 3H), 0.97 (d, 3H), 0.99 (s, 3H), 1.05–2.00 (m, 13H), 2.45 (s, 3H), 3.80 (dd, 1H), 3.96 (dd, 1H), 4.13 (m, 1H), 7.37 (m, 8H), 7.58 (m, 4H), 7.79 (m, 2H).

Preparation 61: 20(S)-formyl-8(S)-(methyldiphenylsilyioxy)-de-A,B-pregnane (compound 80)

Compound 79 (5.80 g) and dry sodium hydrogen-carbonate (908 mg) was dissolved in DMSO (150 ml, previously heated to 150° C. for 10 min and allowed to reach room temperature under argon) and the solution was heated to 110° C. for 90 min. The mixture was cooled to room temperature and worked up. Chromatography (diethyl ether/ pet. ether: 1/20) of the residue yielded the title compound.

NMR: $\delta$=0.62 (s, 3H), 1.06 (s, 3H), 1.09 (d, 3H), 1.05–2.00 (m, 12H), 2.37 (m, 1H), 4.16 (m, 1H), 7.37 (m, 6H), 7.57 (m, 4H), 9.57 (d, 1H).

Preparation 62: 20(S)-chlorocarbonyl-8(S)-(methyldiphenylsilyloxy)-de-A,B-pregnane (compound 81)

Compound 80 (2.97 g) was dissolved in carbon tetrachloride (40 ml) and tert-butyl hypochlorite (1.30 ml) was added at ambient temperature. After stirring for 90 min under argon more tert-butyl hypochlorite (0.50 ml) was added. After additional 90 min the reaction mixture was concentrated in vacuo to yield the title compound. It was immediately used without further purification.

NMR: $\delta$=0.63 (s, 3H), 1.06 (s, 3H), 1.33 (d, 3H), 1.00–2.00 (m, 12H), 2.83 (m, 1H), 4.16 (m, 1H), 7.36 (m, 6H), 7.57 (m, 4H).

Preparation 63: 20(S)-[[ethoxy(thiocarbonyt)thio]-carbonyl]- 8(S)-(methyldiphenylsilyloxy)-de-A,B-pregnane (compound 82)

The crude compound 81 was dissolved in acetone (40 ml) and potassium O-ethyl dithiocarbonate (1.19 g) was added slowly (20 min) while stirring at −30° C. under argon. The temperature was maintained for 1 h and then allowed to reach room temperature. After 3 h altogether the reaction mixture was washed with saturated aqueous sodium hydrogen-carbonate and worked up (dichloromethane). Chromatography (dichloromethane/pet. ether: 1/3) yielded the title compound.

NMR: δ=0.62 (s, 3H), 1.03 (s, 3H), 1.24 (d, 3H), 1.47 (t, 3H), 1.12–1.96 (m, 12H), 2.52 (m, 1H), 4.15 (m, 1H), 4.67 (q, 2H), 7.36 (m, 6H), 7.57 (m, 4H).

Preparation 64: 20(S)/20(R)-[ethoxy(thiocarbonyl)thio]-8(S)-(methyldiphenylsilyloxy)-de-A,B-pregnane (compound 83/84)

Compound 82 (3.23 g) was dissolved in benzene (70 ml) in a pyrex flask under argon. The reaction mixture was heated to 60° C. and was irradiated with UV-light from a high pressure ultraviolet lamp, type TQ760Z2 (Hanau), for 20 min with stirring. The reaction mixture was concentrated in vacuo to yield the title compounds without further purification.

NMR (83): δ=0.63 (s, 3H), 1.14 (s, 3H), 1.42 (t, 3H), 1.47 (d, 3H), 1.00–2.03 (m, 12H), 3.79 (m, 1H), 4.15 (m, 1H), 4.65 (q, 2H), 7.36 (m, 6H), 7.58 (m, 4H).

NMR (84): δ=0.63 (s, 3H), 1.08 (s, 3H), 1.39 (d, 3H), 1.42 (t, 3H), 1.00–2.00 (m, 11H), 2.24 (m, 1H), 3.68 (m, 1H), 4.15 (m, 1H), 4.65 (q, 2H), 7.36 (m, 6H), 7.58 (m, 4H).

Preparation 65: 20(S)/20(R)-[ethoxy(thiocarbonyl)thio]-de-A,B-pregnane- 8(S)-ol (compound 85/86)

To a mixture of compound 83 and 84 (3.06 g) in ethyl acetate (20 ml) was added acetonitrile (10 ml) followed by a 5% solution of hydrofluoric acid in acetonitrile:water, 7:1 (30 ml) under argon and with stirring. Stirring was continued for 1 h at ambient temperature. Saturated aqueous sodium hydrogen-carbonate (100 ml) was added, and the reaction mixture was worked up (ethyl acetate). The residue was purified by chromatography (diethyl ether/pet.ether: 1:3) to yield a mixture of the title compounds.

NMR (85): δ=1.03 (s, 3H), 1.40 (t, 3H), 1.44 (d, 3H), 1.00–2.05 (m, 13H), 3.75 (m, 1H), 4.07 (m, 1H), 4.63 (m, 2H).

NMR (86): δ=0.96 (s, 3H), 1.37 (d, 3H), 1.40 (t, 3H), 1.00–2.05 (m, 12H), 2.22 (m, 1H), 3.63 (m, 1H), 4.07 (m, 1H), 4.63 (m, 2H).

Preparation 66: 20(S)/20(R)-[ethoxy(thiocarbonyl)thio]-de-A,B-pregnane- 8-one (compound 87/88)

DMSO (319 mg), dissolved in dichloromethane (2.0 ml), was added within 5 min to a stirred solution of oxalylchloride (259 mg) in dichloromethane (4.0 ml) at −65° C. under argon. The reaction mixture was stirred for 5 min when a solution of compound 85 and 86 in dichloromethane (2.0 ml) was added within 5 min. Stirring was continued for an additional 15 min. Triethylamine (1.25 ml) was added. The reaction mixture was stirred for 15 min and was then allowed to warm to room temperature. Hydrochloric acid (1N, 15 ml) was added and the reaction mixture was worked up (dichloromethane) to yield a mixture of the title compounds.

NMR (87): δ=0.75 (s, 3H), 1.42 (t, 3H), 1.51 (d, 3H), 1.35–2.56 (m, 12H), 3.79 (m, 1H), 4.65 (q, 2H).

NMR (88): δ=0.69 (s, 3H), 1.41 (d, 3H), 1.43 (t, 3H), 1.35–2.56 (m, 12H), 3.67 (m, 1H), 4.65 (q, 2H).

Preparation 67: 20(S)/20(R)-mercapto-de-A,B-pregnane-8-one (compound 89/90)

To a stirred solution of compound 87 and 88 (512 mg) in dry DMF (15 ml) was added aminoethanol (1.50 ml) under argon. The reaction mixture was worked up (diethyl ether) after 1 h at ambient temperature. The residue was purified by chromatography (diethyl ether/pet.ether: 1:2) to yield a mixture of the title compounds.

NMR (89): δ=0.66 (s, 3H), 1.44 (d, 3H), 1.30–2.62 (m, 13H), 2.93 (m, 1H).

NMR (90): δ=0.70 (s, 3H), 1.37 (d, 3H), 1.30–2.62 (m, 13H), 2.86 (m, 1H).

Preparation 68: Compound 91 and 92
Method: General Procedure 9.
Alkylating agent: 4-Bromo-2-methyl-2-trimethylsilyloxy-butane (0.30 g).

NMR (91): δ=0.09 (s, 9H), 0.70 (s, 3H), 1.21 (s, 6H), 1.28 (d, 3H), 1.00–2.75 (m, 17H).

NMR (92): δ=0.09 (s, 9H), 0.66 (s, 3H), 1.21 (s, 6H), 1.39 (d, 3H), 1.00–2.75 (m, 17H).

Preparation 69: Compound 93 and 94
Method: General Procedure 9.
Alkylating agent: 6-Bromo-2-methyl-2-trimethylsilyloxy-hexane (0.26 g).

NMR (93): δ=0.08 (s, 9H), 0.70 (s, 3H), 1.18 (s, 6H), 1.28 (d, 3H), 1.15–2.25 (m, 21H).

NMR (94): δ=0.08 (s, 9H), 0.66 (s, 3H), 1.18 (s, 6H), 1.38 (d, 3H), 1.15–2.25 (m, 21H).

Preparation 70: Compound 95 and 96
Method: General Procedure 9.
Alkylating agent: 3-(1-methyl-1-[trimethylsilyloxy]ethyl)benzylbromide (0.27 g).

NMR (95): δ=0.09 (s, 9H), 0.44 (s, 3H), 1.31 (d, 3H), 1.55 (s, 6H), 1.20–2.65 (m, 13H), 3.71 (m, 2H), 7.15 (m, 1H), 7.23 (t, 1H), 7.30 (m, 1H), 7.39 (m, 1H).

NMR (96): δ=0.08 (s, 9H), 0.54 (s, 3H), 1.40 (d, 3H), 1.55 (s, 6H), 1.20–2.65 (m, 13H), 3.73 (m, 2H), 7.15 (m, 1H), 7.23 (t, 1H), 7.30 (m, 1H), 7.39 (m, 1H).

Preparation 71: Compound 56 and 57
Method: General Procedure 10.
Starting material: Compound 93 and 94.

NMR (56): δ=0.05 (m, 12H), 0.09 (s, 9H), 0.60 (s, 3H), 0.86 (s, 18H), 1.19 (s, 6H), 1.27 (d, 3H), 1.10–2.12 (m, 19H), 2.20 (dd, 1H), 2.43 (m, 1H), 2.48 (m, 2H), 2.63 (m, 1H), 2.82 (m, 1H), 4.18 (m, 1H), 4.36 (m, 1H), 4.85 (m, 1H), 5.17 (m, 1H), 6.00 (d, 1H), 6.22 (d, 1H).

NMR (57): δ=0.05 (m, 12H), 0.09 (s, 9H), 0.55 (s, 3H), 0.86 (s, 18H), 1.19 (s, 6H), 1.36 (d, 3H), 1.10–2.12 (m, 19H), 2.20 (dd, 1H), 2.43 (m, 1H), 2.48 (m, 2H), 2.63 (m, 1H), 2.82 (m, 1H), 4.18 (m, 1H), 4.36 (m, 1H), 4.85 (m, 1H), 5.17 (m, 1H), 6.00 (d, 1H), 6.22 (d, 1H).

Preparation 72: Compound 58 and 59
Method: General Procedure 10.
Starting material: Compound 95 and 96.

NMR (58): δ=0.05 (m, 12H), 0.08 (s, 9H), 0.39 (s, 3H), 0.86 (s, 9H), 0.87 (s, 9H), 1.29 (d, 3H), 1.56 (s, 6H), 1.15–2.10 (m, 13H), 2.20 (dd, 1H), 2.44 (m, 1H), 2.52 (m, 1H), 2.80 (m, 1H), 3.71 (s, 2H), 4.18 (m, 1H), 4.35 (m, 1H), 4.84 (m, 1H), 5.16 (m, 1H), 5.98 (d, 1H), 6.21 (d, 1H), 7.12–7.34 (m, 3H), 7.40 (m, 1H).

NMR (59): δ=0.05 (m, 12H), 0.08 (s, 9H), 0.45 (s, 3H), 0.86 (s, 9H), 0.87 (s, 9H), 1.38 (d, 3H), 1.56 (s, 6H), 1.15–2.10 (m, 13H), 2.20 (dd, 1H), 2.44 (m, 1H), 2.52 (m, 1H), 2.80 (m, 1H), 3.73 (s, 2H), 4.18 (m, 1H), 4.35 (m, 1H), 4.84 (m, 1H), 5.16 (m, 1H), 5.98 (d, 1H), 6.21 (d, 1H), 7.12–7.34 (m, 3H), 7.40 (m, 1H).

EXAMPLE 1

1(S),3(R)-Dihydroxy-20(R)-(3-ethyl-3-hydroxy-1-pentylthio)-9,10-seco-pregna-5(Z),7(E), 10(19)-triene (Compound 101)

Method: General Procedure 4.
Starting material: Compound 42.

EXAMPLE 2

1(S),3(R)-Dihydroxy-20(S)-(3-ethyl-3-hydroxy-1-pentylthio)-9,10-seco-pregna-5(Z),7(E),10(19)-triene (Compound 102)

Method: General Procedure 4.
Starting material: Compound 43.

EXAMPLE 3

1(S),3(R)-Dihydroxy-20(R)-(4-ethyl-4-hydroxy-1-hexylthio)-9,10-seco-pregna-5(Z),7(E),10(19)-triene (Compound 103)

Method: General Procedure 4.
Starting material: Compound 44.
NMR: δ=0.62 (s, 3H), 0.86 (t, 6H), 1.28 (d, 3H), 1.46 (q, 4H), 1.15–2.10 (m, 20H), 2.32 (dd, 1H), 2.52 (m, 2H), 2.60 (dd, 1H), 2.66 (m, 1H), 2.83 (m, 1H), 4.23 (m, 1H), 4.43 (m, 1H), 5.00 (m, 1H), 5.33 (m, 1H), 6.01 (d, 1H), 6.38 (d, 1H).

EXAMPLE 4

1(S),3(R)-Dihydroxy-20(S)-(4-ethyl-4-hydroxy-1-hexylthio)-9,10-seco-pregna-5(Z),7(E),10(19)-triene (Compound 104)

Method: General Procedure 4.
Starting material: Compound 45.
NMR: δ=0.58 (s, 3H), 0.86 (t, 6H), 1.38 (d, 3H), 1.47 (q, 4H), 1.20–2.15 (m, 20H), 2.31 (dd, 1H), 2.53 (m, 2H), 2.60 (dd, 1H), 2.65 (m, 1H), 2.83 (dd, 1H), 4.23 (m, 1H), 4.43 (m, 1H), 5.00 (m, 1H), 5.33 (m, 1H), 6.02 (d, 1H), 6.37 (d, 1H).

EXAMPLE 5

1(S),3(R)-Dihydroxy-20(R)-(5-ethyl-5-hydroxy-1-heptylthio)-9,10-seco-pregna-5(Z),7(E),10(19)-triene (Compound 105)

Method: General Procedure 4.
Starting material: Compound 46.

EXAMPLE 6

1(S),3(R)-Dihydroxy-20(S)-(5-ethyl-5-hydroxy-1-heptylthio)-9,10-seco-pregna-5(Z),7(E),10(19)-triene (Compound 106)

Method: General Procedure 4.
Starting material: Compound 47.

EXAMPLE 7

1(S),3(R)-Dihydroxy-20(R)-[3-(1-ethyl-1-hydoxypropyl)benzylthio]-9,10-seco-pregna-5(Z),7(E),10(19)-triene (Compound 107)

Method: General Procedure 4.
Starting material: Compound 48.

EXAMPLE 8

1(S),3(R)-Dihydroxy-20(S)-[3-(1-ethyl-1-hydroxypropyl)benzylthio]-9,10-seco-pregna-5(Z),7(E),10(19)-triene (Compound 108)

Method: General Procedure 4.
Starting material: Compound 49.

EXAMPLE 9

1(S),3(R)-Dihydroxy-20(R)-[4-ethyl-4-hydroxy-hex-2-en-1-ylthio]-9,10-seco-pregna-5(Z),7(E),10(19)-triene (Compound 109)

Method: General Procedure 4.
Starting material: Compound 50.

EXAMPLE 10

1(S),3(R)-Dihydroxy-20(S)-[4-ethyl-4-hydroxy-hex-2-en-1-ylthio]-9,10-seco-pregna-5(Z),7(E),10(19)-triene (Compound 110)

Method: General Procedure 4.
Starting material: Compound 51.

EXAMPLE 11

1(S),3(R)-Dihydroxy-20(R)-[4-ethyl-4-hydroxy-hex-2-yn-1-ylthio]-9,10-seco-pregna-5(Z),7(E),10(19)-triene (Compound 111)

Method: General Procedure 4.
Starting material: Compound 52.

EXAMPLE 12

1(S),3(R)-Dihydroxy-20(S)-[4-ethyl-4-hydroxy-hex-2-yn-1-ylthio]-9,10-seco-pregna-5(Z),7(E),10(19)-triene (Compound 112)

Method: General Procedure 4.
Starting material: Compound 53.

EXAMPLE 13

1(S),3(R)-Dihydroxy-20(R)-[4-methyl-4-hydroxy-pent-1-ylthio]-9,10-seco-pregna-5(Z),7(E),10(19)-triene (Compound 113)

Method General Procedure 4.
Starting material: Compound 54.

EXAMPLE 14

1(S),3(R)-Dihydroxy-20(S)-[4-methyl-4-hydroxy-pent-1-ylthio]-9,10-seco-pregna-5(Z),7(E),10(19)-triene (Compound 114)

Method: General Procedure 4.
Starting material: Compound 55.

EXAMPLE 15

1(S),3(R)-Dihydroxy-20(R)-[5-methyl-5-hydroxy-hex-1-ylthio]-9,10-seco-pregna-5(Z),7(E),10(19)-triene (Compound 115)

Method: General Procedure 6.
Starting material: Compound 56.
NMR: δ=0.62 (s, 3H), 1.21 (s, 6H), 1.28 (d, 3H), 1.15–2.15 (m, 22H), 2.31 (dd, 1H), 2.43–2.70 (m, 4H), 2.83 (m, 1H), 4.23 (m, 1H), 4.43 (m, 1H), 5.00 (m, 1H), 5.33 (m, 1H), 6.00 (d, 1H), 6.38 (d, 1H).

EXAMPLE 16

1(S),3(R)-Dihydroxy-20(S)-[5-methyl-5-hydroxy-hex-1-ylthio]-9,10-seco-pregna-5(Z),7(E),10(19)-triene (Compound 116)

Method: General Procedure 6.
Starting material: Compound 57.
NMR: δ=0.58 (s, 3H), 1.22 (s, 6H), 1.38 (d, 3H), 1.15–2.15 (m, 22H), 2.31 (dd, 1H), 2.50–2.70 (m, 4H), 2.83 (m, 1H), 4.23 (m, 1H), 4.44 (m, 1H), 5.00 (m, 1H), 5.33 (m, 1H), 6.02 (d, 1H), 6.37 (d, 1H).

EXAMPLE 17

1(S),3(R)-Dihydroxy-20(R)-[3-(1-methyl-1-hydroxyethyl)benzylthio]-9,10-seco-pregna-5(Z),7(E),10(19)-triene (Compound 117)

Method: General Procedure 4.
Starting material: Compound 58.
NMR: δ=0.41 (s, 3H), 1.30 (d, 3H), 1.57 (s, 6H), 1.15–2.10 (m, 16H), 2.30 (dd, 1H), 2.40–2.65 (m, 2H), 2.81 (m, 1H), 3.73 (m, 2H), 4.22 (m, 1H), 4.42 (m, 1H), 4.97 (m, 1H), 5.31 (m, 1H), 5.97 (d, 1H), 6.35 (d, 1H), 7.15–7.38 (m, 3H), 7.48 (m, 1H).

EXAMPLE 18

1(S),3(R)-Dihydroxy-20(S)-[3-(1-methyl-1-hydroxyethyl)benzylthio]-9,10-seco-pregna-5(Z),7(E),10(19)-triene (Compound 118)

Method: General Procedure 4.
Starting material: Compound 59.
NMR: δ=0.49 (s, 3H), 1.40 (d, 3H), 1.58 (s, 6H), 1.15–2.10 (m, 16H), 2.30 (dd, 1H), 2.56 (m, 1H), 2.58 (dd, 1H), 2.81 (m, 1H), 3.75 (m, 2H), 4.22 (m, 1H), 4.42 (m, 1H), 4.98 (m, 1H), 5.32 (m, 1H), 5.99 (d, 1H), 6.35 (d, 1H), 7.15–7.38 (m, 3H), 7.46 (m, 1H).

EXAMPLE 19

1(S),3(R)-Dihydroxy-20(R)-[4-methyl-4-hydroxy-pent-2-en-1-ylthio]-9,10-seco-pregna-5(Z),7(E),10(19)-triene (Compound 119)

Method: General Procedure 4.
Starting material: Compound 60.

EXAMPLE 20

1(S),3(R)-Dihydroxy-20(S)-[4-methyl-4-hydroxy-pent-2-en-1-ylthio]-9,10-seco-pregna-5(Z),7(E),10(19)-triene (Compound 120)

Method: General Procedure 4.
Starting material: Compound 61.

EXAMPLE 21

1(S),3(R)-Dihydroxy-20(R)-[4-methyl-4-hydroxy-pent-2-yn-1-ylthio]-9,10-seco-pregna-5(Z),7(E),10(19)-triene (Compound 121)

Method: General Procedure 4.
Starting material: Compound 62.

EXAMPLE 22

1(S),3(R)-Dihydroxy-20(S)-[4-methyl-4-hydroxy-pent-2-yn-1-ylthio]-9,10-seco-pregna-5(Z),7(E),10(19)-triene (Compound 122)

Method: General Procedure 4.
Starting material: Compound 63.

EXAMPLE 23

1(S),3(R)-Dihydroxy-20(R)-(5-ethyl-5-hydroxy-1-heptyl-(R)-sulfinyl)-9,10-seco-pregna-5(Z),7(E),10(19)-triene (Compound 123)

Method: General Procedure 4.
Starting material: Compound 64.

EXAMPLE 24

1(S),3(R)-Dihydroxy-20(R)-(5-ethyl-5-hydroxy-1-heptyl-(S)-sulfinyl)-9,10-seco-pregna-5(Z),7(E),10(19)-triene (Compound 124)

Method: General Procedure 4.
Starting material: Compound 65.

EXAMPLE 25

1(S),3(R)-Dihydroxy-20(S)-(5-ethyl-5-hydroxy-1-heptyl-(R)-sulfinyl)-9,10-seco-pregna-5(Z),7(E),10(19)-triene (Compound 125)

Method: General Procedure 4.
Starting material: Compound 66.

EXAMPLE 26

1(S),3(R)-Dihydroxy-20(S)-(5-ethyl-5-hydroxy-1-heptyl-(S)-sulfinyl)-9,10-seco-pregna-5(Z),7(E),10(19)-triene (Compound 126)

Method: General Procedure 4.
Starting material: Compound 67.

EXAMPLE 27

1(S),3(R)-Dihydroxy-20(R)-(5-ethyl-5-hydroxy-1-heptylsulfonyl)-9,10-seco-pregna-5(Z),7(E),10(19)-triene (Compound 127)

Method: General Procedure 5.
Starting material: Compound 68.

EXAMPLE 28

1(S),3(R)-Dihydroxy-20(S)-(5-ethyl-5-hydroxy-1-heptylsulfonyl)-9,10-seco-pregna-5(Z),7(E),10(19)-triene (Compound 128)

Method: General Procedure 5.
Starting material: Compound 69.

EXAMPLE 29

1(S),3(R)-Dihydroxy-20(R)-[3-(1-methyl-1-hydroxyethyl)benzyl-(R)-sulfinyl]-9,10-seco-pregna-5(Z),7(E),10(19)-triene (Compound 129)

Method: General Procedure 4.
Starting material: Compound 70.

EXAMPLE 30

1(S),3(R)-Dihydroxy-20(R)-[3-(1-methyl-1-hydroxyethyl)benzyl-(S)-sulfinyl]-9,10-seco-pregna-5(Z),7(E),10(19)-triene (Compound 130)

Method: General Procedure 4.
Starting material: Compound 71.

EXAMPLE 31

1(S),3(R)-Dihydroxy-20(S)-[3-(1-methyl-1-hydroxyethyl)benzyl-(R)-sulfinyl]-9,10-seco-pregna-5(Z),7(E)10(19)-triene (Compound 131)

Method: General Procedure 4.
Starting material: Compound 72.

EXAMPLE 32

1(S),3(R)-Dihydroxy-20(S)-[3-(1-methyl-1-hydroxyethyl)benzyl-(S)-sulfinyl]-9,10-seco-pregna-5(Z),7(E),10(19)-triene (Compound 132)

Method: General Procedure 4.
Starting material: Compound 73.

EXAMPLE 33

1(S),3(R)-Dihydroxy-20(R)-[3-11-methyl-1-hydroxyethyl)benzylsulfonyl]-9,10-seco-pregna-5(Z),7(E),10(19)-triene (Compound 133)

Method: General Procedure 5.
Starting material: Compound 74.

EXAMPLE 34

1(S),3(R)-Dihydroxy-20(S)-[3-(1-methyl-1-hydroxyethyl)benzylsulfonyl]-9,10-seco-pregna-5(Z),7(E),10(19)-triene (Compound 134)

Method: General Procedure 5.
Starting material: Compound 75.

EXAMPLE 35

1(S),3(R)-Dihydroxy-20(R)-(3-methyl-3-hydroxy-1-butylthio)-9,10-seco-pregna-5(Z),7(E),10(19)-triene (Compound 135)

Method: General Procedure 5.
Starting material: Compound 76.
NMR: $\delta$=0.62 (s, 3H), 1.24 (s, 6H), 1.30 (d, 3H), 1.10–2.10 (m, 18H), 2.31 (dd, 1H), 2.45 (m, 1H), 2.61 (m, 2H), 2.70 (m, 1H), 2.82 (m, 1H), 4.23 (m, 1H), 4.43 (m, 1H), 5.00 (m, 1H), 5.33 (m, 1H), 6.01 (d, 1H), 6.38 (d, 1H).

EXAMPLE 36

1(S),3(R)-Dihydroxy-20(S)-(3-methyl-3-hydroxy-1-butylthio)-9,10-seco-pregna-5(Z),7(E),10(19)-triene (Compound 136)

Method: General Procedure 5.
Starting material: Compound 77.
NMR: $\delta$=0.58 (s, 3H), 1.25 (s, 6H), 1.39 (d, 3H), 1.20–2.10 (m, 18H), 2.31 (dd, 1H), 2.59 (m, 1H), 2.63 (m, 2H), 2.69 (m, 1H), 2.83 (m, 1H), 4.23 (m, 1H), 4.44 (m, 1H), 4.99 (m, 1H), 5.33 (m, 1H), 6.02 (d, 1H), 6.36 (d, 1H).

EXAMPLE 37

Capsules containing Compound 103

Compound 103 was dissolved in arachis oil to a final concentration of 1 μg/ml oil. Ten parts by weight of gelatine, 5 parts by weight of glycerin, 0.08 parts by weight potassium sorbate, and 14 parts by weight distilled water were mixed together with heating and formed into soft gelatine capsules. These were then filled each with 100 μl of the oily solution of Compound 103.

EXAMPLE 38

Dermatological Cream containing Compound 103

Compound 103 (0.05 mg) was dissolved in almond oil (1 g). To this solution was added mineral oil (40 g) and self-emulsifying beeswax (20 g). The mixture was heated to liquifidation. After the addition of hot water (40 ml), the mixture was mixed well. The resulting cream contains approximately 0.5 μg of compound 103 per gram of cream.

What we claim is:
1. A compound of the formula I

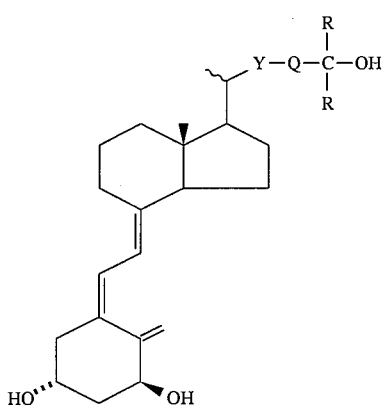

in which formula Y is sulfur, S(O), or S(O)$_2$; R stands for C$_1$–C$_3$ alkyl; or

can form a C$_3$–C$_8$ carbocyclic ring; Q is a C$_1$–C$_8$ hydrocarbylene diradical; and prodrugs of I in which one or more of the hydroxy groups are masked as groups which can be reconverted to hydroxy groups in vivo.

2. A compound of formula I according to claim 1 in which Y is sulfur and Q is C$_2$–C$_4$-alkylene.

3. A stereoisomer of a compound according to claim 1 having a side chain with the S-configuration at C-20.

4. A stereoisomer of a compound according to claim 1 having a side chain with the R-configuration at C-20.

5. A compound according to claim 1 which is a) 1(S),3(R)-Dihydroxy-20(R)-(4-ethyl-4-hydroxy-1-hexylthio)-9,10-seco-pregna-5(Z),7(E),10(19)-triene, b) 1(S),3(R)-Dihydroxy-20(R)-[5-methyl-5-hydroxy-1-hexylthio]- 9,10-seco-pregna-5(Z),7(E),10(19)-triene, c) 1(S),3(R)-Dihydroxy-20(R)-[3-(1-methyl-1-hydroxy-ethyl)benzylthio]- 9,10-seco-pregna-5(Z),7(E),10(19)-triene, or d) 1(S),3(R)-Dihydroxy-20(R)-(3-methyl-3-hydroxy-1-butylthio)-9,10-seco-pregna-5(Z),7(E),10(19)-triene.

6. A method for producing a compound of formula I of claim 1 comprising a) reacting a 1(S),3(R)-bis-(hydroxy-protected)-20(S)-formyl- 9,10-secopregna-5(Z),7(E),10(19)-triene with tert-butyl hypochlorite to form a product of formula 2

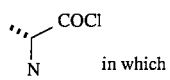 in which

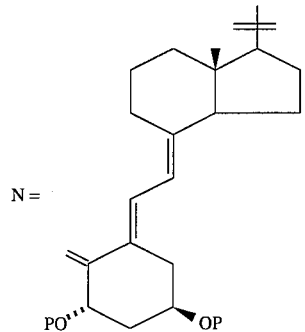

and O-P is a protected hydroxy group b) substituting a compound of formula 2 with potassium O-ethyl dithiocarbonate to form a product of formula 3

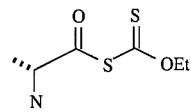

in which N has the above meaning;

c) subjecting a compound of formula 3 to a photochemical reaction in benzene in which the initially produced acyl-radical is decarbonylated at the appropriate temperature to form alkyl radicals which preferentially combine with the O-ethyl dithiocarbonate radicals to form the two C-20 isomers having the formulas 4 and 5

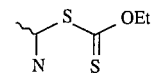

in which N has the above meaning;

d) treating a compound of formula 4 or 5, or a mixture thereof, with aminoethanol to form the thiols having formula 6 or 7, or a mixture thereof,

in which N has the above meaning;

e) reacting a compound of formula 6 or 7, or a mixture thereof, with a base and the requisite alkylating agent IV; in which R stands for C$_1$–C$_3$ alkyl; or

can form a C$_1$–C$_3$ carbocyclic ring; Q is a C$_1$–C$_8$ hydrocarbylene diradical; Z is a hydroxy protecting group or a hydroxy group; T is an appropriate leaving group

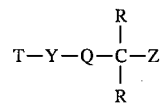

in a solvent to give a product of the formula II as a mixture of the two C-20 isomers or as the enantiomerically pure forms

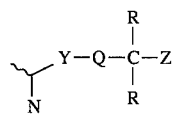

in which N, Y, Q, Z and R have the above meanings;

f) subjecting a compound of formula II to the arbitrary sequence of isomerization with UV-light in the presence of triplet sensitizer and removal of the protective groups with hydrofluoric acid or tetra-n-butylammonium fluoride to form the desired compound of formula I of claim 1 in enantiomeric pure form or as a stereoisomeric mixture.

7. A method for producing a compound of formula I of claim 1 comprising a) reacting a hydrindane having the following formula

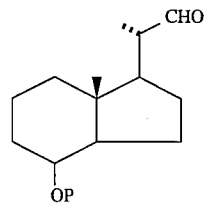

in which O-P is a protected hydroxy group;

a) with tert-butyl hypochlorite to form the corresponding acid chloride, b) substituting the acid chloride product of a) with potassium O-ethyl dithiocarbonate to give a compound of the formula 82

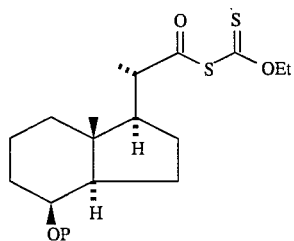

in which O-P is a protected hydroxy group;

c) subjecting a compound of formula 82 to a photochemical reaction in benzene in which the initially produced acyl-radical is decarbonylated at the appropriate temperature to form alkyl radicals which preferentially combine with the O-ethyl dithiocarbonate radicals to form the two C-20 isomers with the formulas 83 and 84

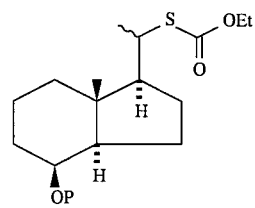

in which O-P has the above meaning;

d) deprotecting a compound of formula 83 or 84, or a mixture thereof, with hydrofluoric acid or tetra-n-butylammonium fluoride) to form the corresponding hydroxy compounds, e) oxidizing the hydroxy compound formed in d) with a dimethylsulfoxide reagent to form the corresponding ketones;

f) treating the ketones formed in e) with aminoethanol to form the thiols having formulas 89 or 90, or a mixture thereof;

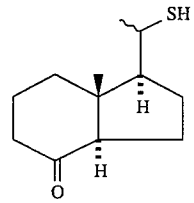

g) reacting a compound of formula 89 or 90, or a mixture thereof, with base and the requisite alkylating agent of formula IV of claim 6 in a solvent to give a product of the formula V as a mixture of the isomers or as the enantiomerically pure forms

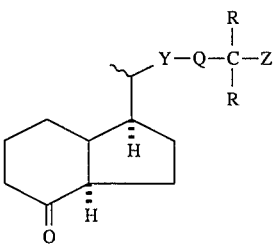

in which Y, Q, Z and R are defined in claim 6;

h) coupling a compound of formula V, or a mixture thereof, with the anion of [1Z,3S,5R]-[2-[3,5-bis-[tert-butyldimethylsilyloxy]-2-methylenecyclohexylidene]ethyl]diphenylphosphine oxide in an Horner-Wittig reaction to form a product of the formula III as a mixture of stereoisomers or as the enantiomerically pure forms

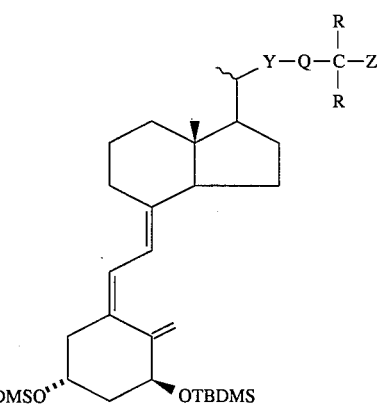

in which Y, Q, Z and R have the meanings given in claim 6;

i) deprotecting a compound of the formula III, or a mixture thereof, with tetra-n-butylammonium fluoride or hydrofluoric acid to form the desired compound of formula I of claim 1 in enantiomeric pure form or as a stereoisomeric mixture.

8. A pharmaceutical composition containing an effective amount of one or more of the compounds of one of claims 1–5, together with pharmaceutically acceptable, non-toxic carriers.

9. A pharmaceutical composition according to claim 8 in dosage unit form containing from 0.1 ppm to 0.1% by weight of the dosage unit of a compound of formula I.

10. A method for treating diseases characterized by abnormal cell differentiation and/or cell proliferation by administering to a patient in need thereof an effective amount of a composition according to claim 8.

11. A method of claim 10 wherein the disease is psoriasis.

12. A method of treating acne by administering to a patient in need thereof an effective amount of a composition according to claim 8.

13. A method for promoting osteogenesis and treating osteoporosis by administering to a patient in need thereof an effective amount of a composition according to claim 8.

* * * * *